(12) United States Patent
Navarrini et al.

(10) Patent No.: US 8,648,217 B2
(45) Date of Patent: Feb. 11, 2014

(54) MODIFICATION OF CARBONACEOUS MATERIALS

(75) Inventors: Walter Navarrini, Boffalora Ticino Milan (IT); Maurizio Sansotera, Milan (IT); Pierangelo Metrangolo, Pioltello (IT); Pietro Cavallotti, Milan (IT); Giuseppe Resnati, Monza (IT)

(73) Assignee: Solvay Solexis S.p.A., Bollate (IT)

( * ) Notice: Subject to any disclaimer, the term of this patent is extended or adjusted under 35 U.S.C. 154(b) by 681 days.

(21) Appl. No.: 12/671,895

(22) PCT Filed: Aug. 4, 2008

(86) PCT No.: PCT/EP2008/060210
§ 371 (c)(1),
(2), (4) Date: Feb. 2, 2010

(87) PCT Pub. No.: WO2009/019243
PCT Pub. Date: Feb. 12, 2009

(65) Prior Publication Data
US 2011/0190544 A1    Aug. 4, 2011

(30) Foreign Application Priority Data
Aug. 7, 2007  (EP) .................................. 07113955

(51) Int. Cl.
*C07C 41/44* (2006.01)
*C07C 43/12* (2006.01)

(52) U.S. Cl.
CPC .................................. *C07C 43/126* (2013.01)
USPC ...................................................... 568/615

(58) Field of Classification Search
None
See application file for complete search history.

(56) References Cited

U.S. PATENT DOCUMENTS

| | | | |
|---|---|---|---|
| 3,442,942 A | 5/1969 | Sianesi et al. | |
| 3,650,928 A | 3/1972 | Sianesi et al. | |
| 3,665,041 A | 5/1972 | Sianesi et al. | |
| 3,715,378 A | 2/1973 | Belardinelli et al. | |
| 3,847,978 A | 11/1974 | Sianesi et al. | |
| 4,451,646 A | 5/1984 | Sianesi et al. | |
| 4,500,739 A * | 2/1985 | Caporiccio et al. | 568/677 |
| 5,000,830 A | 3/1991 | Marchionni et al. | |
| 5,114,092 A | 5/1992 | Gelardi | |
| 5,155,282 A * | 10/1992 | Marchionni et al. | 568/615 |
| 5,258,110 A | 11/1993 | Sianesi et al. | |
| 5,326,823 A | 7/1994 | Rolando et al. | |
| 5,744,651 A | 4/1998 | Marchionni et al. | |
| 2003/0148161 A1 | 8/2003 | Nuber et al. | |
| 2005/0192413 A1 | 9/2005 | Marchionni et al. | |

FOREIGN PATENT DOCUMENTS

| | | | |
|---|---|---|---|
| EP | 1454938 A1 | 9/2004 | |
| EP | 1524287 A1 | 4/2005 | |
| JP | 03045606 A | 2/1991 | |
| JP | 03056506 A | 3/1991 | |
| JP | 03234706 A | 10/1991 | |
| JP | 04277586 A | 10/1992 | |
| JP | 05078419 A | 3/1993 | |
| WO | WO 2006023921 A2 | 3/2006 | |
| WO | WO 2006023922 A2 | 3/2006 | |

OTHER PUBLICATIONS

Zhou Z.-B. et al., "Modification of polystyrene via aromatic per(poly)fluoroalkylation by per(poly) fluorodiacyl peroxides", Journal of fluorine chemistry, 1996, vol. 79, p. 1-5, Elsevier Science S.A.; 6 pgs.

Kawase T. et al., "Surface modification of silk fabric with perfluoroalkanoyl peroxides" (lang.: Japanese), Sen'i Gakkaishi, 1995, vol. 51(2), p. 86-94, CAS 123:172469; 1 pg AWASE.

Kawase T. et al., "Novel Fluoroalkylation of Polyester Surfaces: Grafting with Perfluoroalkanoyl Peroxides", Textile Research Journal, 1994, vol. 64 (7), p. 375-380, SAGE publication ; 6 pgs.

Sawada H. et al., "Synthesis and properties of poly(carbonates) possessing fluoroalkyl groups on the aromatic nuclei" (lang.: Japanese), Zairyo Gijutsu (1997), 15(2), 35-39, CAS 126:251555; 1 pg.

Zhou Z.-B. et al., "Modification of linear triblock copolymer SBS via olefinic per(poly)fluoroalkylation by per(poly) fluorodiacyl peroxides", Journal of Fluorine Chemistry, 2000, vol. 104(2), p. 285-290, Elsevier Science S.A.; 6 pgs.

Zhou Z.-B. et al., "Modification of SBS polymers by perfluoroalkylation" (lang.: Chinese), Yingyong Huaxue, 2000, vol. 17(5), p. 516-519, CAS 134:57090; 1 pg.

He, H.-Y. et al., "Surface perfluorofunctionalization of polystyrene and styrene-butadiene- styrene block copolymer by perfluorodiacyl peroxides", Journal of Fluorine Chemistry, 2000, vol. 106(2),p. 117-120, Elsevier Science S.A. ; 4 pgs.

Hayakawa Y. et al., "Trifluoromethylation by bis(trifluoroacetyl) peroxide of polymers bearing benzene rings", Polymer, 2001, vol. 42(9), p. 4081-4086, Elsevier ; 6 pgs.

(Continued)

*Primary Examiner* — Rosalynd Keys
(74) *Attorney, Agent, or Firm* — Arent Fox LLP

(57) ABSTRACT

A modified carbonaceous material having chemically bound on its surface at least one fluoropolyoxyalkylene chain (chain $R_f$) and a process for the modification of a carbonaceous material [material (C)]. The process comprises: contacting the material (C) with a (per)fluoropolyether peroxide comprising at least one peroxidic moiety comprised between $sp^3$ carbon atoms and at least one fluoropolyoxyalkene chain (chain $R_f$), i.e. a fluorocarbon segment comprising ether linkages in main chain [peroxide (P)]; and heating the material (C) while in contact with the peroxide (P) at a temperature exceeding decomposition temperature of the peroxide (P).

6 Claims, 1 Drawing Sheet

(56) References Cited

OTHER PUBLICATIONS

He, H.-Y. et al., "Radical addition reaction between perfluoro- and ω-H-perfluorodiacyl peroxides and C60 synthesis of perfluoro- and ω-H-perfluoroalkylated C60" (lang.: Chinese), Huaxue Xuebao, 2003, vol. 61(5), p. 736-741, CAS 139:214202; 1 pg.

Sawada H. et al., "Reactions of fluoroalkanoyl peroxides with single-walled carbon nanotubes: application to sidewall modification of single-walled carbon nanotubes with the introduction of fluoroalkyl groups", Polymers for Advanced Technologies, 2006, vol. Date 2005, vol. 16(11-12), p. 764-769, John Wiley & Sons, Inc.; 6 pgs.

* cited by examiner

MODIFICATION OF CARBONACEOUS MATERIALS

CROSS-REFERENCE TO RELATED APPLICATIONS

This application is a U.S. national stage application under 35 U.S.C. §371 of International Application No. PCT/EP2008/060210 filed Aug. 4, 2008, which claims priority to European Patent Application No. 07113955.4 filed Aug. 7, 2007, these applications being incorporated herein by reference in their entirety for all purposes.

TECHNICAL FIELD

The present invention pertains to a process for the modification of carbonaceous materials with (per)fluoropolyether chains for their oil- and water-repellence surface modification. The invention also pertains to carbonaceous materials obtained from said process.

BACKGROUND ART

Carbonaceous materials are commonly used additives and fillers which exhibit interesting structural, mechanical, electrical and electromechanical properties and which have found application in a wide variety of field.

Nevertheless, their application has been found in some cases somewhat limited due to the difficulty in dispersing and compatibilizing such materials with different media, in particular fluorinated phases, due to their inadequate surface hydrophilicity.

From this point of view, much attention has been devoted both on surface modification of said materials by means of surface agents and on covalent functionalization by introduction of fluoroalkyl group on the surface.

Fluoroalkanoyl peroxides have been used in the past as convenient tool for the introduction of the corresponding fluoroalkyl group on carbonaceous materials.

Thus, WO 2006/23921 (DUPONT) 2 Mar. 2006 discloses the functionalization of carbonaceous materials, in particular of fullerenes or curved carbon nanostructures with low molecular weight perfluorodiacyl peroxide of formula [Z—[CF$_2$]$_d$—O$_c$—[CF$_2$—CFR]$_b$—O$_a$—[CF$_2$]$_e$—CO—O]$_2$, with a=0 or 1, b=0 to 10, c=0 or 1, d=1 to 10, e=1 to 10. Examples relate to the reaction of bis(perfluoro-2-propoxypropanoyl)peroxide of formula C$_3$F$_7$OCF(CF$_3$)—C(O)—OO—C(O)—CF(CF$_3$)OC$_3$F$_7$ with single-walled carbon nanotubes.

SAWADA, Hideo, et al. Reactions of fluoroalkanoyl peroxides with single-walled carbon nanotubes: application to sidewall modification of single-walled carbon nanotubes with the introduction of fluoroalkyl groups. *Polymers for advanced technologies*. 2005, vol. 16, p. 764-769. disclose the reaction of perfluorodiacyl peroxides of formula:

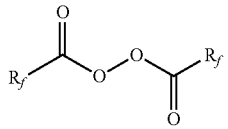

wherein R$_f$=—CF(CF$_3$)OC$_3$F$_7$ or —CF(CF$_3$)OC$_4$F$_9$.

Nevertheless, the processes of the prior art, involving fluorinated perfluoroalkanoyl peroxides, require handling of unstable and potentially explosive low molecular weight fluorinated acyl peroxides.

Moreover the processes of the prior art do not enable accessing functionalization of carbonaceous materials with polymeric fluorooxyalkylene groups. Those groups are of particular interest as they exhibit surface active characteristics which cannot be achieved with low molecular weight counterparts and efficiently modify oil- and water-repellence of the carbonaceous materials surface.

There is thus a current shortfall in the art for a process for the effective functionalization of carbonaceous materials with fluorinated peroxides of increased thermal and storage stability and for functionalized materials thereof having oil- and water-repellence and low-surface energy properties.

DISCLOSURE OF INVENTION

Figure 1:
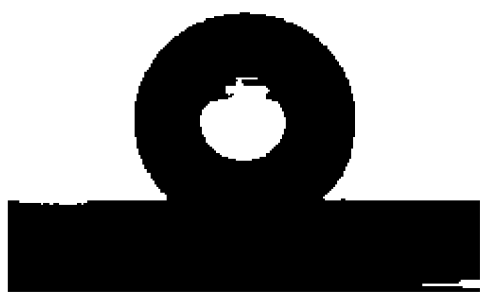
FIG. 1 shows a drop of water on the surface of a pressed pellet.

The invention thus pertains to a process for the modification of a carbonaceous material [material (C)], said process comprising:

contacting the material (C) with a (per)fluoropolyether peroxide comprising at least one peroxidic moiety comprised between sp$^3$ carbon atoms and at least one fluoropolyoxyalkene chain (chain R$_f$), i.e. a fluorocarbon segment comprising ether linkages in main chain [peroxide (P)];

heating the material (C) while in contact with the peroxide (P) at a temperature exceeding decomposition temperature of said peroxide (P).

The Applicant has surprisingly found that the process as above detailed advantageously enables efficient surface modification of the carbonaceous material, by chemical grafting of fluoropolyoxyalkene chain(s) onto the surface of the carbonaceous material, so that oil- and water-repellence of this latter are significantly increased.

The (per)fluoropolyether peroxide of the process of the invention is advantageously endowed with increased thermal and storage stability, so that it can be easily handled and stored with no risk of explosion.

Within the context of the present invention, the expressions "carbonaceous material" and "material (C)" are intended to denote all those materials which essentially consist of carbon. It is understood that said carbonaceous materials might comprise reduced amounts of other elements (e.g. H, O, N, S . . . ), without this significantly affecting the physicochemical properties of the carbonaceous material itself.

Among carbonaceous materials suitable for the purposes of the invention, mention can be notably made of carbon black, carbon fibers, diamond like carbon, graphite, fullerenes, including spherical fullerenes and carbon nanotubes.

The expression "carbon black" is intended to denote powdered form of highly dispersed, amorphous elemental carbon. Carbon black is generally available as a finely divided, colloidal material in the form of spheres and their fused aggregates. Types of carbon black are characterized by the size distribution of the primary particles, and the degree of their aggregation and agglomeration. Average primary particle diameters of carbon black typically range from 10 to 400 nm, while average aggregate diameters range from 100 to 800 nm.

Carbon black can be manufactured under controlled conditions whereas soot is randomly formed, and they can be distinguished on the basis of tar, ash content and impurities. Carbon black can be also made by the controlled vapor-phase pyrolysis and/or thermal cracking of hydrocarbon mixtures such as heavy petroleum distillates and residual oils, coal-tar products, natural gas and acetylene. The expression "carbon black" thus embraces notably acetylene black, channel black, furnace black, lamp black, thermal black. Acetylene black is the type of carbon black derived from the burning of acetylene. Channel black is made by impinging gas flames against steel plates or channel irons (from which the name is derived), from which the deposit is scraped at intervals. Furnace black is the term generally applied to carbon black made in a refractory-lined furnace. Lamp black, the properties of which are markedly different from other carbon blacks, is made by burning heavy oils or other carbonaceous materials in closed systems equipped with settling chambers for collecting the solids. Thermal black is produced by passing natural gas through a heated brick checkerwork where it thermally cracks to form a relatively coarse carbon black. Over 90% of all carbon black produced today is furnace black. Carbon black is available commercially from numerous suppliers such as Cabot Corporation.

The expression "Diamond-like carbon (DLC)", as used therein, encompasses all forms of amorphous carbon materials containing significant amounts (e.g. >50%) of $sp^3$ hybridized carbon atoms. As a result, DLC materials typically display some of the unique properties of natural diamond. It is well-known that natural diamond can be found in two crystalline polytypes. The usual one has its carbon atoms arranged in a cubic lattice, while the very rare one (lonsdaleite) has a hexagonal lattice. In DLC materials, these polytypes are typically present at the nanoscale level of structure, so that DLC coatings can be made that at the same time are amorphous, flexible, and yet purely $sp^3$ bonded "diamond". The hardest, strongest, and slickest is such a mixture, known as tetrahedral amorphous carbon, or ta-C. For example a coating of only 2 μm thickness of ta-C increases the resistance of common (ie. type 304) stainless steel against abrasive wear; changing its lifetime in such service from one week to 85 years. Such ta-C can be considered to be the "pure" form of DLC, since it consists only of $sp^3$ bonded carbon atoms. Fillers such as hydrogen, graphitic $sp^2$ carbon, and metals are generally used in the other forms of DLC to reduce production expenses, but at the cost of decreasing the service lifetimes of the articles being coated. The various forms of DLC can be applied to almost any material that is compatible with a vacuum environment.

The term "graphite" is intended to denote the low density allotrope of carbon (C), whose structure consists of layered hexagonal rings of $sp^2$-hybridised carbon atoms. These layers are notably held together by weak Van der Waals type forces resulting from the interactions between clouds of delocalised p electrons from each of the layers.

The term "fullerene" encompasses carbon molecules (notably different from graphite and diamond), consisting of a spherical, ellipsoid, or cylindrical arrangement of carbon atoms bound by $sp^2$ bonds, under the form of predominant linked hexagonal rings of carbon atoms, but also pentagonal or sometimes heptagonal rings that prevent said assembly from being planar.

Spherical fullerenes are often called "buckyballs" whereas cylindrical fullerenes are known as "buckytubes", or "carbon nanotubes (CNT)".

Either single-walled carbon nanotubes (SWCN) or multi-walled carbon nanotubes (MWCN) can be used to the purpose of the invention. CNTs may have diameters ranging from about 0.6 nanometers (nm) for a single-wall carbon nanotube (SWNT) up to 3 nm, 5 nm, 10 nm, 30 nm, 60 nm or 100 nm for a SWNT or a multiple-wall carbon nanotube (MWNT). A CNT may range in length from 50 nm up to 1 millimeter (mm), 1 centimeter (cm), 3 cm, 5 cm, or greater. A CNT will typically have an aspect ratio of the elongated axis to the other dimensions greater than about 10. In general, the aspect ratio is between 10 and 2000.

Preferably the material (C) is chosen among carbon black and/or DLC.

Carbon blacks obtainable by the process of the invention are particularly suitable for increasing their compatibility in host matrices having low surface tension, i.e. for dispersing in fluoropolymer matrices, and the like.

DLC materials obtainable by the process of the invention are particularly interesting because they add to the intrinsic outstanding mechanical properties of the DLC the advantages of a fluorinated surface, including increased affinity towards fluorinated lubricating media so as to improve their tribological behaviour.

The expression "at least one peroxide moiety" is understood to mean that the peroxide (P) comprises one or more than one peroxide moiety. Herein below, the expression "peroxide (P)" shall be understood both in the singular and in the plural.

The peroxide moiety of the peroxide (P) is comprised between $sp^3$ hybridized carbon atoms: thanks to this layout, thermal and storage stability of the peroxide (P) is advantageously increased over, notably, that of perfluoroalkanoyl peroxides, wherein the —OO— group is bound to –C(O)-$sp^2$ hybridized carbon atoms.

The fluoropolyoxyalkene chain ($R_f$) of the peroxide (P) is preferably a chain comprising repeating units $R^o$, said repeating units being chosen among the group consisting of:
(i) —CFXO—, wherein X is F or $CF_3$,
(ii) —CFXCFXO—, wherein X, equal or different at each occurrence, is F or $CF_3$, with the provision that at least one of X is —F,
(iii) —$CF_2CF_2CF_2O$—,
(iv) —$CF_2CF_2CF_2CF_2O$—,
(v) —$(CF_2)_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being chosen among the followings: —CFXO—, —$CF_2$CFXO—, —$CF_2CF_2CF_2O$—, —$CF_2CF_2CF_2CF_2O$—, with each of each of X being independently F or $CF_3$. and $T_3$ being a $C_1$-$C_3$ perfluoroalkyl group.

Preferably the peroxide moieties of the peroxide (P) of the invention are randomly distributed in the perfluoropolyoxyalkylene chain.

Thus, the peroxide (P) preferably complies with formula (I) here below:

$$C-O-(CFX^1O)_{c1}(CFX^2CFX^3O)_{c2}(CF_2CF_2CF_2O)_{c3}(CF_2CF_2CF_2O)_{c4}(O)_p-C' \qquad \text{formula (I)}$$

wherein
$X^1$, $X^2$, $X^3$ are equal or different from each other and at each occurrence are independently —F, —$CF_3$;
C and C', equal to or different from each other, are independently selected from —$CF_3$, —$CF_2$—$CF_3$, —$CF_2$Cl, —$CF_2CF_2$Cl, —$CF_2$—COF, —COF;
c1, c2 c3, and c4, equal or different from each other, are independently integers ≥0, such that and c1+c2+c3+c4 is in the range 5 to 2000, preferably between 10 and 500; should at least two of c1, c2, c3 and c4 be different from zero, the different recurring units are generally statistically distributed along the chain;

p is an integer >0.

Typically the peroxide (P) is chosen such that the ratio p/(c1+c2+c3+c4) is comprised between 0.001 and 0.9, preferably between 0.01 and 0.5.

The peroxidic PFPEs can be prepared, for example, by photoassisted polymerization of tetrafluoroethylene (TFE) and/or hexafluoropropene (HFP), in the presence of oxygen according to the teachings of U.S. Pat. No. 3,442,942 (MONTEDISON SPA) 6 May 1969, U.S. Pat. No. 3,650,928 (MONTEDISON SPA) 21 Mar. 1972, U.S. Pat. No. 3,665,041 (MONTEDISON SPA) 23 May 1972.

The peroxidic PFPEs containing the units —(CF$_2$)—CFZ—O— can be prepared, for example, according to what described in U.S. Pat. No. 5,114,092 by polymerization, in the presence of oxygen and UV, of one or more (per)fluoroalkylvinylethers of formula CF$_2$=CFOXa wherein Xa is one or more groups (R'O)$_m$R'', equal to or different from each other, wherein m=0-6, R' is selected from the groups —CF$_2$—, —CF$_2$CF$_2$—, —CF$_2$CF(CF$_3$)—, R'' is selected from C$_1$-C$_{10}$ linear perfluoroalkyl, or C$_3$-C$_{10}$ branched perfluoroalkyl, or C$_3$-C$_{10}$ cyclic perfluoroalkyl, by operating in the presence of solvent and at a temperature not higher than 50° C. This same process can be carried out also in the presence of TFE and/or HFP. See furthermore, for example, EP 1454938 A (SOLVAY SOLEXIS SPA) 8 Sep. 2004, EP 1524287 A (SOLVAY SOLEXIS SPA) 20 Apr. 2005.

Preferably the peroxide (P) is selected from the following classes:

(A) Xo-O(CF$_2$CF$_2$O)$_{r1}$(CF$_2$O)$_{s1}$(O)$_{t1}$—Xo'    formula (II-A)

wherein

Xo and Xo', equal to or different from each other, are —CF$_2$Cl, —CF$_2$CF$_2$Cl, —CF$_3$, —CF$_2$CF$_3$, —CF$_2$COF, —COF;

r1, s1, t1 are integers ≥0 such that the number average molecular weight is between 400 and 150,000, preferably between 500 and 80 000; t1 is an integer >0; both r1 and s1 are preferably different from zero, with the ratio r1/s1 being preferably comprised between 0.1 and 10;

Peroxides (P) complying with formula (IIA) here above can be prepared by tetrafluoroethylene oxypolymerization notably following the teachings of U.S. Pat. No. 3,715,378 (MONTEDISON SPA) 6 Feb. 1973, U.S. Pat. No. 4,451,646 (MONTEDISON SPA) 29 May 1984, U.S. Pat. No. 5,258,110 (AUSIMONT SRL) 2 Nov. 1993, U.S. Pat. No. 5,744,651 (AUSIMONT SPA) 28 Apr. 1998.

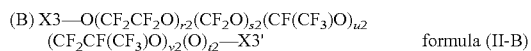
(B) X3—O(CF$_2$CF$_2$O)$_{r2}$(CF$_2$O)$_{s2}$(CF(CF$_3$)O)$_{u2}$
(CF$_2$CF(CF$_3$)O)$_{v2}$(O)$_{t2}$—X3'    formula (II-B)

wherein:

X3 and X3', equal to or different from each other, are —CF$_2$Cl, —CF$_2$CF$_2$Cl, —CF$_2$CF$_3$, —CF$_3$, —C$_3$F$_7$, —CF(CF$_3$)COF, —COF, —CF$_2$COF, —CF$_2$C(O)CF$_3$;

r2, s2, u2, v2 are integers ≥0, chosen so that the number average molecular weight is between 500 and 150 000, preferably between 700 and 80 000; t2 is an integer >0. Preferably r2, s2, u2, v2 are all >0, with the ratio v2/(r2+s2+u2) being <1.

Peroxides (P) complying with formula (II-B) here above can be prepared by oxypolymerization of tetrafluoroethylene and hexafluoropropylene notably following the teachings of U.S. Pat. No. 5,000,830 (AUSIMONT SRL) 19 Mar. 1991 and U.S. Pat. No. 3,847,978 (MONTEDISON SPA) 12 Nov. 1974;

(C) X2-O(CF$_2$CF$_2$O)$_{r3}$(CF$_2$O)$_{s3}$(CF$_2$(CF$_2$)$_w$CF$_2$O)$_{k3}$
(O)$_{t3}$X2'    formula (II-C)

wherein:

X2 and X2', equal to or different from each other, are —CF$_2$COF, —COF;

w=1 or 2;

r3, s3, and k3 are integers ≥0 chosen so that the number average molecular weight is between 500 and 100,000 and t3 is an integer >0; preferably r3, s3 and k3 are all >0, with the ratio r3/s3 being typically between 0.2 and 10, and the ratio k3/(r3+s3) being generally lower than 0.05.

Peroxides (P) complying with formula (II-C) above can be prepared following teachings of US 2005192413 (SOLVAY SOLEXIS SPA) 1 Sep. 2005.

More preferably, peroxide (P) complies with formula (III) here below:

A-O—(CF$_2$O)$_{a1}$(CF$_2$CF$_2$O)$_{a2}$(O)$_{a3}$-A'    formula (III)

wherein:

A and A', equal or different from each other and at each occurrence are independently selected from —CF$_3$, —CF$_2$—CF$_3$, —CF$_2$Cl, —CF$_2$CF$_2$Cl, —CF$_2$—COF;

a1, a2 and a3 are integers >0 such that the number average molecular weight is between 400 and 150,000, preferably between 500 and 80 000, with the ratio a2/a1 being comprised between 0.1 and 10, more preferably between 0.2 and 5; preferably the ratio a3/(a1+a2+1) is comprised between 0.01 and 0.5, more preferably between 0.03 and 0.3.

The process of the invention can be carried out in the presence of suitable solvents, wherein the material (C) can be suspended. These solvents are chosen among those which do not react with the peroxide (P). Among suitable solvents mention can be notably made of (per)fluorocarbon, (per)chlorofluorocarbon, (per)(halo)fluoroalkylethers, tertiary (per) fluoroalkylamines, (per)fluoropolyethers, liquefied gases like supercritical CO$_2$.

Contact time between material (C) and peroxide (P) is not particularly limited and will be chosen by the skilled in the art in relation, notably, with the reaction temperature; contact time can vary between a few seconds and several hours; it is nevertheless understood that this contact time is generally comprised between 15 minutes and 50 hours, preferably between 30 minutes and 30 hours.

It is also generally preferred to contact material (C) and peroxide (P) under inert atmosphere, i.e. under an atmosphere substantially free from oxygen. Typically, material (C) and peroxide (P) are contacted in the presence of an inert gas, like notably nitrogen, argon, helium, gaseous fluorocarbons, gaseous hydrofluorocarbon, gaseous (per)fluoroethers (e.g. CF$_4$, CF$_3$CH$_2$F, CF$_3$OCF$_2$CF$_3$) or, as an alternative, under reduced pressure.

The material (C) while in contact with peroxide (P) can be heated at a temperature comprised between 40° C. and 300° C.; appropriate temperature will be selected by the skilled in the art with reference to the decomposition temperature of peroxide (P). Preferably, temperatures suitable for achieving efficient decomposition of peroxide (P) and thus radical reaction with the carbonaceous material are those comprised between 100 and 250° C., more preferably between 120 and 240° C.

Another object of the invention is a modified carbonaceous material comprising chemically bound on its surface fluoropolyoxyalkene chain (R$_f$) as above described.

Said materials can be obtained by the process of the invention.

The Applicant has surprisingly found that the modified carbonaceous material as above described is permanently modified, so that surface properties, e.g. hydro- and oleo-repellence, are definitively modified.

The carbonaceous material preferably comprises chemically bound on its surface fluoropolyoxyalkylene chains of formula:

$$-(O)_w-(CFX^1O)_{c1}(CFX^2CFX^3O)_{c2}(CF_2CF_2CF_2O)_{c3}(CF_2CF_2CF_2CF_2O)_{c4}-E,$$

wherein:
w is zero or 1;
X1, X2, X3, c1, c2, c3, c4 have the same meaning as above defined;
E is a group selected from $-CF_3$, $-CF_2-CF_3$, $-CF_2Cl$, $-CF_2CF_2Cl$, $-CF_2-COF$, $-CF_2OCOF$, or is a group bonding though an ether linkage the surface of the carbonaceous material.

The Applicant thinks, without this limiting the scope of the invention, that the fluoropolyoxyalkylene chains are mainly bound to the carbonaceous materials via a carbon-carbon covalent bond, that is to say that in above depicted formula, w is zero. This behaviour is considered to be linked to the relative instability of oxygen radicals on fluoropolyoxyalkylene chains, so that a carbon radical is generally formed by evolution of $COF_2$ before the radical species can react with the carbonaceous material.

Nevertheless, carbonaceous materials wherein the fluoropolyoxyalkylene chains is bound through an oxygen atom (w=1) might exist and are still encompassed by the scope of present invention.

The carbonaceous material more preferably comprises chemically bound on its surface fluoropolyoxyalkylene chains of formula:

$$-(O)_w-(CF_2O)_{a1}(CF_2CF_2O)_{a2}-A''$$

wherein:
w is zero or 1;
a1, a2 have the same meaning as above defined;
A'' is a group selected from $-CF_3$, $-CF_2-CF_3$, $-CF_2Cl$, $-CF_2CF_2Cl$, $-CF_2-COF$, or is a group bonding though an ether linkage the surface of the carbonaceous material.

The invention will be described in more detail with reference to the following examples whose purpose is merely illustrative and not intended to limit the scope of the invention.

Example 1

In a glass reactor having an inner volume of 100 ml, were introduced 0.5 gr of CABOT VULCAN® XC72R carbon black and suspended in 20 ml of $CF_3OCFClCF_2Cl$(diluent); 1 g of a perfluoropolyether peroxide of formula: $CF_3-O-(CF_2O)_{a1}(CF_2CF_2O)_{a2}(O)_{a3}-CF_3$, having a a2/a1 molar ratio of 1.15, a number average molecular weight of 29 400, and a P.O. value of 1.33, was then added drop wise under vigorous stirring. Reactor temperature was brought at 40° C. under nitrogen bubbling until complete evaporation of the diluent, so as to ensure an oxygen-free environment.

Figure 2:
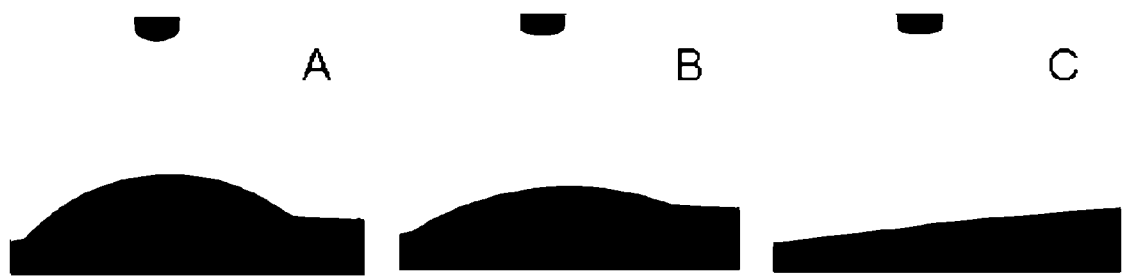
FIGS. 2A-2C show a comparative pressed pellet of carbon black with immediate absorption of a water drop.

The reaction mixture was then heated at 150° C.; temperature was then raised stepwise by 15° C. at once, keeping each incremented temperature constant for 1 hour, until reaching 195° C. Finally, the mixture was maintained at 200° C. for 2 hours. Then the reactor was evacuated and kept under reduced pressure for 6 hours at high temperature (210° C.). Solid residue was then rinsed with water (3×50 ml) and $CF_3OCFClCF_2Cl$ (3×50 ml), by stirring the treated material with the appropriate amount of diluent at room temperature for 1 hour. Sample is finally dried under vacuum (0.01 mmHg) and high temperature (210° C.) during 6 hours. EDS analysis of the treated sample showed a peak in the region around 0.7 KeV, which is due to the presence of fluorine. XPS analysis of the treated sample showed a peak in the region of 690 eV, associated to the presence of C—F bonds. A pellet of treated material was obtained by press moulding under a load of 7 000 kg/cm² a small amount of treated sample. So obtained pellet was used for determining contact angle with water. FIG. 1 depicts a drop of water on the surface of above mentioned pressed pellet: a contact angle of 145° was determined, which remained stable with time (water was not absorbed nor spread). As a comparison, a pressed pellet of CABOT VULCAN® XC72R carbon black underwent in similar conditions immediate absorption of a water drop, as shown by the sequence of images of FIG. 2. It was thus not possible to determine contact angle.

Example 2

Same procedure as described in example 1 was repeated but using a sample of a film of DLC.

Figure 3:
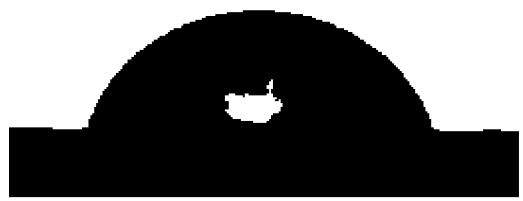
FIG. 3 shows a drop of n-dodecane on the surface of a treated sample.

At the end of the treatment, the sample was analysed by XPS and contact angle with both water and n-dodecane. XPS analysis showed a peak centered at 689 eV, typical of C—F bonds. FIG. 3 depicts a drop of n-dodecane on the surface of the treated sample: a contact angle of 72° was determined, which remained stable with time (n-dodecane was not absorbed nor spread).

Comparative Example 3

Isobutyryl Peroxide

Similar procedure as in example 1 was followed but using isobutyryl peroxide (8.6 ml of a solution containing 4.2% wt of isobutyryl peroxide in $CF_3OCFClCF_2Cl$) instead of the perfluoropolyether peroxide, in combination with 48 mg of CABOT VULCAN® XC72R carbon black. The reaction mixture was heated at 55° C. during 48 hours. The treated sample is rinsed with an aqueous solution of NaHCO3 (2% wt) and water before drying. Contact angle with water, determined following same procedure as in example 1, showed for this sample a value lower by roughly 10° than those observed in example 1, thus demonstrating a poorer hydrophobicity.

The invention claimed is:
1. A process for the modification of a carbonaceous material (C), said carbonaceous material consisting essentially of carbon, said process comprising:
contacting said material (C) with a (per)fluoropolyether peroxide comprising at least one peroxidic moiety comprised between sp³ carbon atoms and at least one fluoropolyoxyalkene chain (chain $R_f$); and
heating said material (C) while in contact with said peroxide (P) at a temperature exceeding decomposition temperature of said peroxide (P),
wherein the material (C) is selected from the group consisting of carbon black, carbon fibers, diamond-like carbon (DLC), graphite, and fullerenes,
wherein the peroxide (P) complies with formula (III) here below:

$$A-O-(CF_2O)_{a1}(CF_2CF_2O)_{a2}(O)_{a3}-A' \qquad \text{formula (III)}$$

wherein:
A and A', equal or different from each other and at each occurrence are independently selected from the group consisting of —$CF_3$, —$CF_2$—$CF_3$, —$CF_2Cl$, —$CF_2CF_2Cl$, and —$CF_2$—COF;

a1, a2 and a3 are integers >0 such that the number average molecular weight is between 400 and 150,000, with the ratio a2/a1 being comprised between 0.1 and 10 and the ratio a3/(a1+a2+1) is comprised between 0.01 and 0.5.

2. The process according to claim 1, wherein said material (C) is selected from the group consisting of carbon black and Diamond-like carbon (DLC).

3. The process according to claim 1, wherein said material (C) while in contact with peroxide (P) is heated at a temperature between 40° C. and 300° C.

4. The process according to claim 1, wherein the number average molecular weight is between 500 and 80000.

5. The process according to claim 1, wherein the ratio a2/a1 is between 0.2 and 5.

6. The process according to claim 1, wherein the ratio a3/(a1+a2+1) is between 0.03 and 0.3.

* * * * *